United States Patent [19]

Yong et al.

[11] 4,452,900

[45] * Jun. 5, 1984

[54] METHOD FOR DETERMINING CLAY CONTENT IN TAILINGS AND SLUDGE

[75] Inventors: Raymond N. Yong; Amar J. Sethi, both of Beaconsfield, Canada

[73] Assignee: Suncor, Inc., Toronto, Canada

[*] Notice: The portion of the term of this patent subsequent to Oct. 25, 2000 has been disclaimed.

[21] Appl. No.: 312,606

[22] Filed: Oct. 19, 1981

[30] Foreign Application Priority Data

Nov. 21, 1980 [CA] Canada ................................. 365173

[51] Int. Cl.³ ...................... G01N 33/24; G01N 31/16
[52] U.S. Cl. ...................................... 436/72; 436/163
[58] Field of Search .......... 23/230 R, 230 M, 230 EP; 436/79, 163, 75

[56] References Cited

U.S. PATENT DOCUMENTS 3,273,967 9/1966 Wilson ............................ 23/230 EP
3,607,078 9/1971 Dietert et al. .................... 23/230 R
3,836,330 9/1974 Melachrinos ............... 23/230 EP X

OTHER PUBLICATIONS

API RP 13B, First Edition, 1962, by American Petroleum Institute.
Mauser et al., J. Amer. Chem. Soc., vol. 62, pp. 1811–1814, 1940.
Page, Soil Science, vol. 51, pp. 133–140, 1941.

Primary Examiner—Arnold Turk
Attorney, Agent, or Firm—Paul Lipsitz

[57] ABSTRACT

A method for estimating the content of clay or clay minerals in the tailings or sludge resulting from the extraction of bitumen from tar sands and similar materials by titrating the tailings or sludge with methylene blue.

5 Claims, 3 Drawing Figures

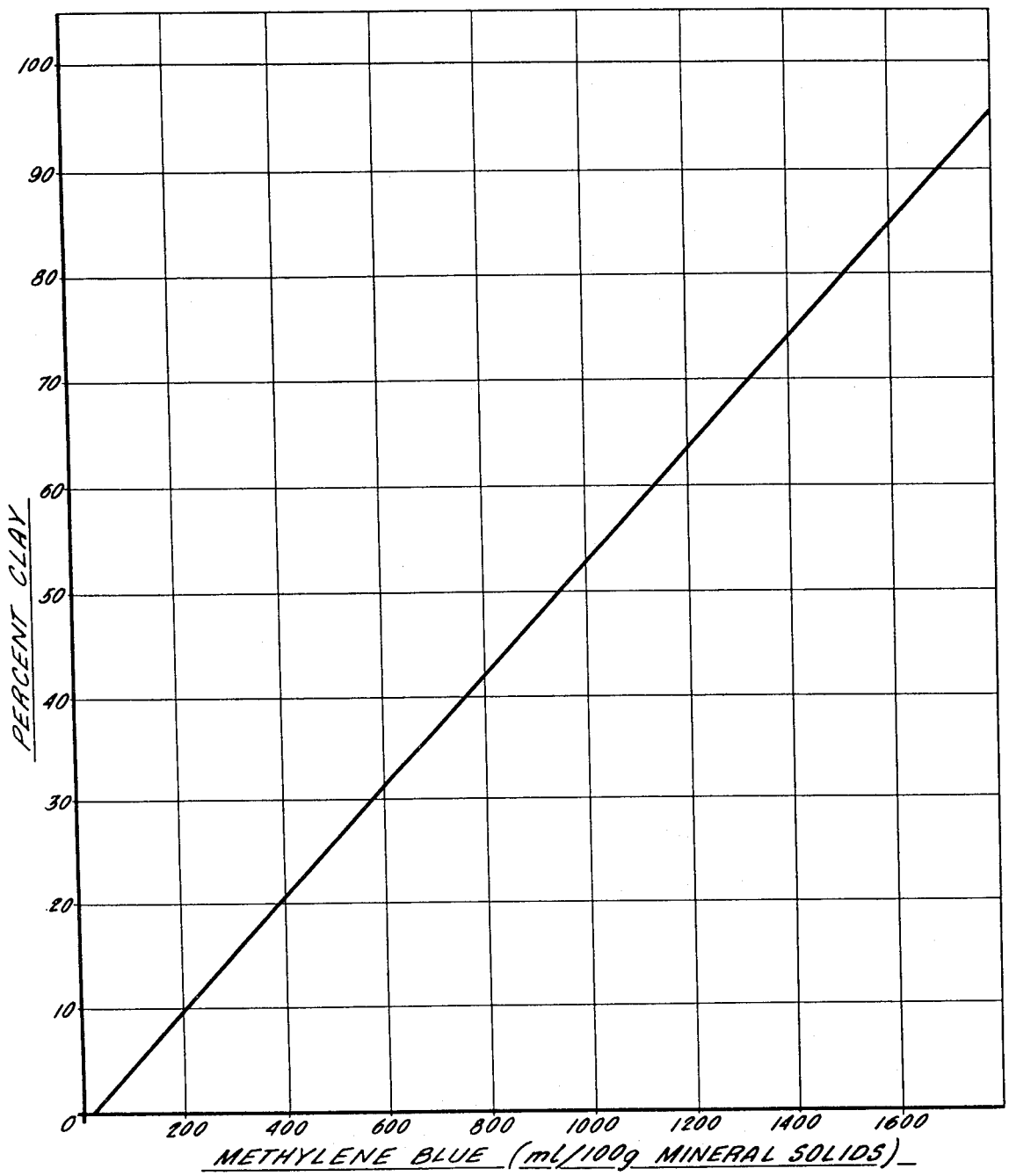

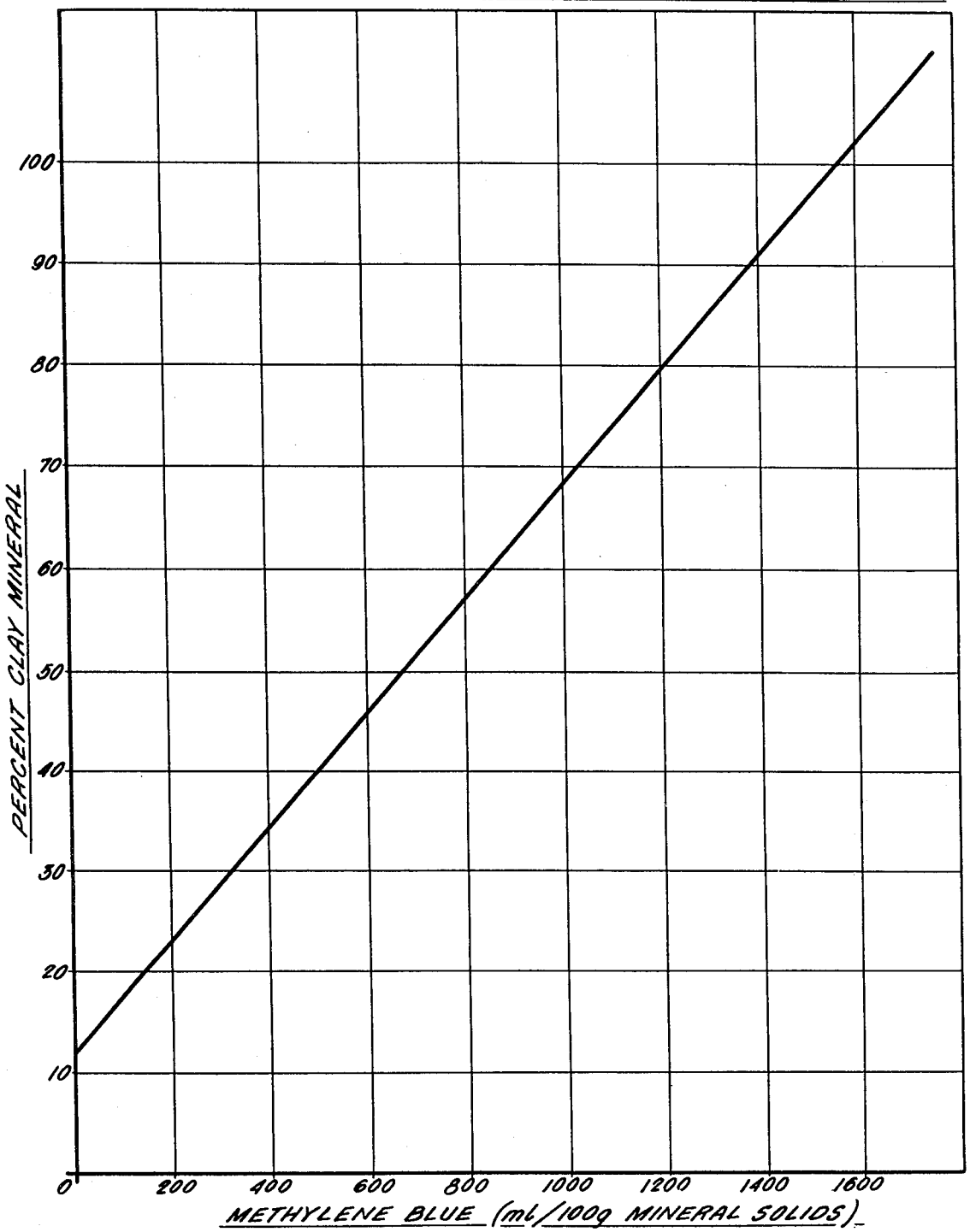

METHOD FOR DETERMINING CLAY CONTENT IN TAILINGS AND SLUDGE

In the hot water process for recovery of bitumen from tar sands and similar materials, a large volume of sand tailings are generated. These tailings comprise fine solids of clay or clay minerals which require a very long time to settle, forming a tar sand tailings sludge. The volumes of tailings and the resulting sludge are very large and it is necessary to know the content of clay and/or clay minerals present in the particular tailings being generated during processing so that the amount of sludge which will eventually form and its volume can be determined in order to provide for adequate storage of the material. This calculation can readily be made since at equilibrium a constant clay minerals to water ratio of 0.31 seems to be maintained with sludge. In the presently available methods of analysis it is necessary to (a) use a sedimentation-centrifugation technique which requires a very long time (e.g., about one week) for each determination to be made or (b) oven drying, solvent extraction and x-ray diffraction for determination of minerals and clay minerals in the sludge. Similar techniques are required for planning of tar sands mining for bitumen extraction. All these techniques are time consuming whereas the present invention provides a routine method which can be accomplished in just a few minutes whereby the mineral content in tailings or sludge can be estimated by deaired density measurements and titration with a cationic dye, i.e. methylene blue. These estimations are made through an empirical correlation technique which has been developed since the complex nature of the tailings, sludge or tar sand deposits from a compositional point of view render exact methods of determination of mineral contents most difficult and tedious.

It is known in the art that color reactions occur between clays and amines (J.A.C.S. 62 p. 1811–14, 1940). These color changes provide a basis for the use of benzidene as a test for montmorillonite, although it has been reported that benzidene is not specific for the reaction and that the iron present also contributes to color development (Soil Sci. 51 133–140, 1941). It is also known that methylene blue may be used to estimate the cation exchange capacity of drilling mud solids or clays (bentonite) and this technique is a standard American Petroleum Institute method (API-RP-13B, 1st Edition).

As indicated above, in the method of the present invention an empirical correlation is established relating the amount of methylene blue adsorbed by the clay or clay mineral to the amount of clay and/or clay mineral present in the tailings or sludge.

FIG. 2 is an empirical curve used in the invention relating the amount of methylene blue used to percent clay in the material analyzed; and FIG. 3 is an empirical curve used in the invention relating the amount of methylene blue used to percent clay mineral in the material analyzed.

Figure 1:
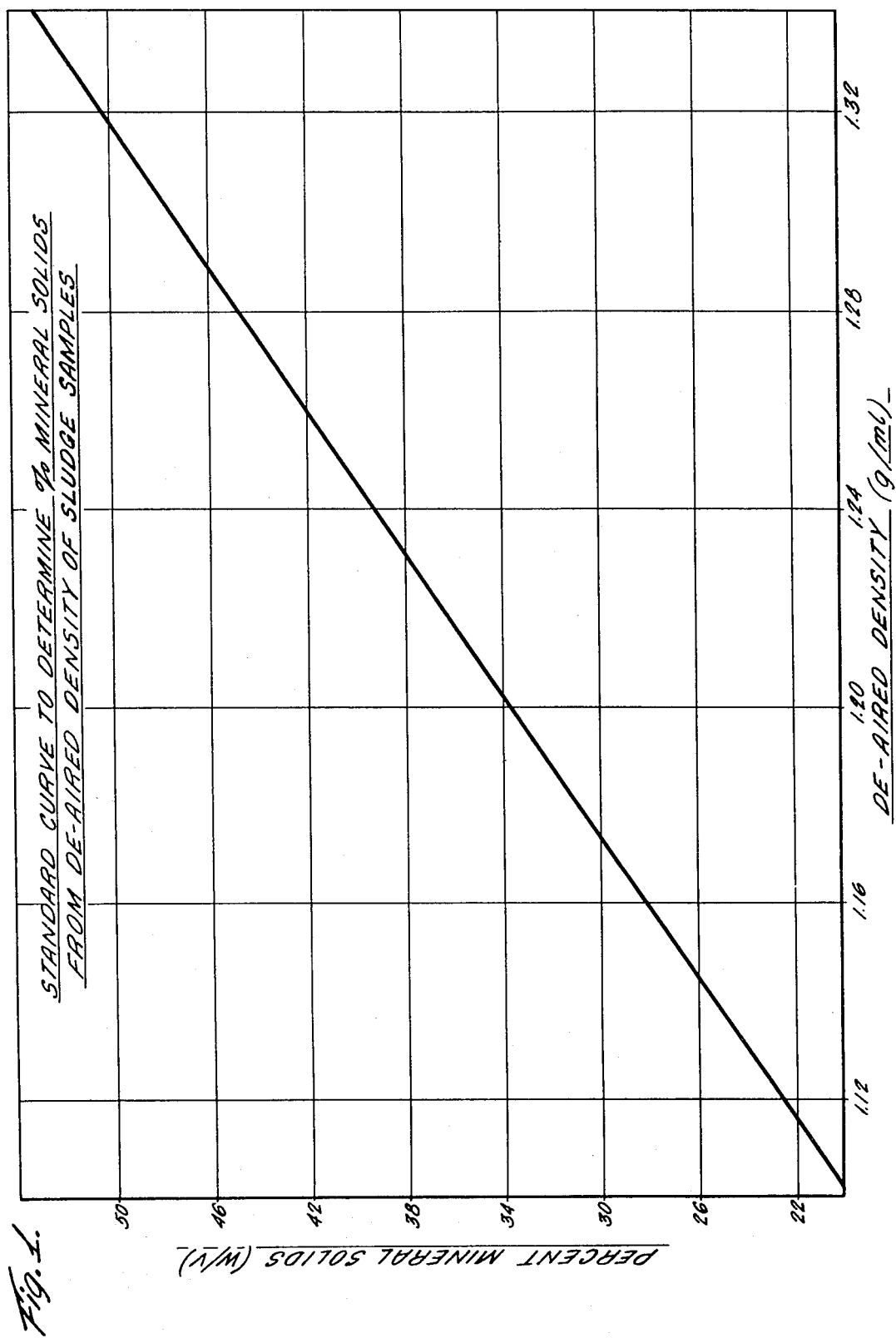
FIG. 1 is an empirical curve used in the invention to relate desired density of the material analyzed to percent mineral solids contained in the material.

Methylene blue dye is adsorbed on clay mineral surfaces by a cation exchange reaction and, in accord with the present invention, the clay is acidified prior to titration so that the clay surfaces will be of constant surface charge and so that the amorphous $Fe_2O_3$ will attain positive surface charge and thus not absorb any cationic dye. Therefore, adsorption will take place only on permanent exchange sites which are due to isomorphic substitution in clay minerals. Because of their low cation exchange capacity, the non-clay materials present (i.e., quartz, feldspar, calcite, etc.) do not absorb the methylene blue dye and thus the amount of methylene blue dye adsorbed by the tailings or sludge samples is directly related to the amount of clay minerals present. The method of the invention will be illustrated by use of a sludge sample, although, of course, a tailings sample or even a bitumen sample may be used for actual analysis. The method follows:

A known weight of sludge ($5\pm1$ g) is taken dispersed in about 50 ml water and acidified with 2 ml of 10% $H_2SO_4$. This solution is titrated in 1 ml increments to the end point with methylene blue dye (0.01N).

The end point is reached when the sample has absorbed all the dye possible, and the excess passed into the water solution. This point is visualized by placing a drop of the sludge suspension on filter paper by means of the blunt end a 1 ml pipette. Before the excess is reached, a blue dot is formed, surrounded by a wet, colorless, circular area. When an excess of dye is attained, the blue color begins to extend into the wet area. The excess must remain after two minutes of shaking the titrated sample to ensure complete absorption.

In order to establish empirical curves with which to correlate the methylene blue titration with clay or clay mineral content, a direct determination of percent clay or clay mineral is made with the particular type of sludge to be analyzed. In order to estimate the clay or clay minerals in the tailings or sludge it is necessary to first establish their minerals content and relate this to deaired density. FIG. 1 shows such a curve where actual mineral content was obtained by the oven drying technique. The procedure for obtaining deaired solids and preparing the empirical curves for the methylene blue titration follows:

1. The exact volume of a 25-ml pycnometer is determined by weighing empty and filled with distilled water.
2. A sample sludge is deaired under vacuum (74 cm Hg) for one hour.
3. The deaired sludge is carefully poured into the pycnometer and weighed—thus the weight and volume of the sludge are known.
4. The density is calculated:

$$\text{density} = \frac{\text{weight (g)}}{\text{volume (ml)}}$$

5. From the relationship of de-aired density to percent mineral solids (w/v) given in FIG. 1, the amount of mineral solids in the sludge sample is found. The slope of this linear relationship may be somewhat different than theoretically expected, because of the presence of small amounts of dissolved or free gases still retained in the samples, even after deairing.

6. Several samples of a known volume or weight of sludge are taken to contain approximately 1–2 g mineral solids (as determined in step 5), acidified and titrated with methylene blue as described above.

6. The amount of methylene blue required per 100 g mineral solids versus the amount of clay present ($<2\mu$ diameter) in the mineral fraction as determined by the sedimentation-certrifugation technique, is plotted to obtain the standard curve shown in FIG. 2. Similarly the amount of clay minerals as determined by the x-ray diffraction technique versus the amount of methylene blue used may be plotted to obtain FIG. 3. These correlation curves are plotted from the analysis of numerous tailings and sludge samples. About 200 samples were analyzed to obtain the data in FIG. 2 and FIG. 3.

8. Samples with unknown content of clay or clay minerals may then be titrated with methylene blue and the clay or clay mineral content obtained from the curves.

The method of the invention, while not giving completely accurate values, provides a means for estimating the clay or clay mineral content of the tailings, sludge, or bitumen. The estimated values obtained are of great value in permitting calculations to be made to estimate the volumes of containment necessary for the total sludge to be generated over time and, in conjunction with other parameters determined separately, allows other valuable information to be obtained, e.g., time for settlement of fines in the tailings, total volume of settled particles, etc. The following table illustrates the kinds of results the method of the invention provides for tar sands samples mined prior to their processing for bitumen extraction with the hot water process:

| Sample | Actual % Clay* | Estimated % Clay from FIG. 2 (Methylene Blue Method) |
|---|---|---|
| 1 | 19.3 | 19.3 |
| 2 | 22.3 | 18.5 |
| 3 | 21.4 | 18.6 |
| 4 | 21.3 | 21.0 |

*Determined by sedimentation centrifugation technique.

The invention claimed is:

1. A method for estimating the content of clay or clay minerals in a material comprised of tar sands bitumen, or tailings or sludge therefrom which comprises
    (a) preparing an empirical curve relating deaired density of said material to percent mineral solids of raw material
    (b) titrating acidified samples of said material containing a known amount of mineral solids as determined by the curve prepared in step (a) with methylene blue to an end point showing no further absorption of said methylene blue and
    (c) comparing the amount of methylene blue absorbed per unit of mineral solids with an empirical curve relating said amount of methylene blue to clay or clay mineral content.

2. The method of claim 1 where clay minerals content in tar sands tailings is determined.

3. The method of claim 1 wherein clay minerals content of sludge is determined.

4. The method of claim 1 wherein clay content of tar sands tailings is determined.

5. The method of claim 1 wherein clay content of sludge is determined.

* * * * *